United States Patent [19]
Briggs, III

[11] Patent Number: 5,839,437
[45] Date of Patent: Nov. 24, 1998

[54] ENDOTRACHEAL TUBE ANTI-DISCONNECT DEVICE

[76] Inventor: Stephen W. Briggs, III, P.O. Box 1503, Orangevale, Calif. 95662

[21] Appl. No.: 959,551

[22] Filed: Oct. 28, 1997

[51] Int. Cl.$^6$ .............................. A61M 16/00; A62B 9/06
[52] U.S. Cl. ............ 128/207.17; 128/912; 128/DIG. 26; 128/207.14
[58] Field of Search ......................... 128/207.17, 200.26, 128/DIG. 26, 912, 207.14, 202.27

[56] References Cited

U.S. PATENT DOCUMENTS

| | | | |
|---|---|---|---|
| 3,039,469 | 6/1962 | Fountain | 128/207.17 |
| 3,927,676 | 12/1975 | Schultz | 128/207.17 |
| 5,282,463 | 2/1994 | Hammersley | 128/912 |
| 5,357,952 | 10/1994 | Schuster et al. | 128/207.17 |
| 5,368,023 | 11/1994 | Wolf | 128/207.17 |

*Primary Examiner*—Kimberly L. Asher
*Attorney, Agent, or Firm*—Donald E. Nist

[57] ABSTRACT

The improved endotracheal anti-disconnect device includes a flexible, resilient elongated patient neck band having a main body, the front surface of which bears a number of hook-receiving loops. The band has narrow opposite ends which form tabs, the front surfaces of which bear a number of hooks. With this arrangement the tabs can be passed through slots in the sides of an endotracheal tube bracket and then can be reflected rearwardly and connected by the hooks to the loops to releasably hold the bracket against the throat of a patient. The device also includes a ring assembly having a ring with a central space and to which ring are connected 4 connectors, which radiate therefrom. Two of the connectors are in the form of wings which are disposed horizontally and are elongated. The wings bear a number of hooks on their inner surfaces so that the ring can be pulled against the bracket and connected by the wings to the front surface of the neck band. The ring fits over the front-to-rear portion of an endotracheal tube, holding that portion securely in place. Upper and lower vertically extending arms are the other two connectors. The front surface of one arm bears hook-receiving loops while the rear surface of the arm bears hooks. With this arrangement, the arms can be wound around the transverse portion of the endotracheal tube to support it in place and prevent its rotation. Preferably, the ring assembly and neck band are of plastic.

4 Claims, 2 Drawing Sheets

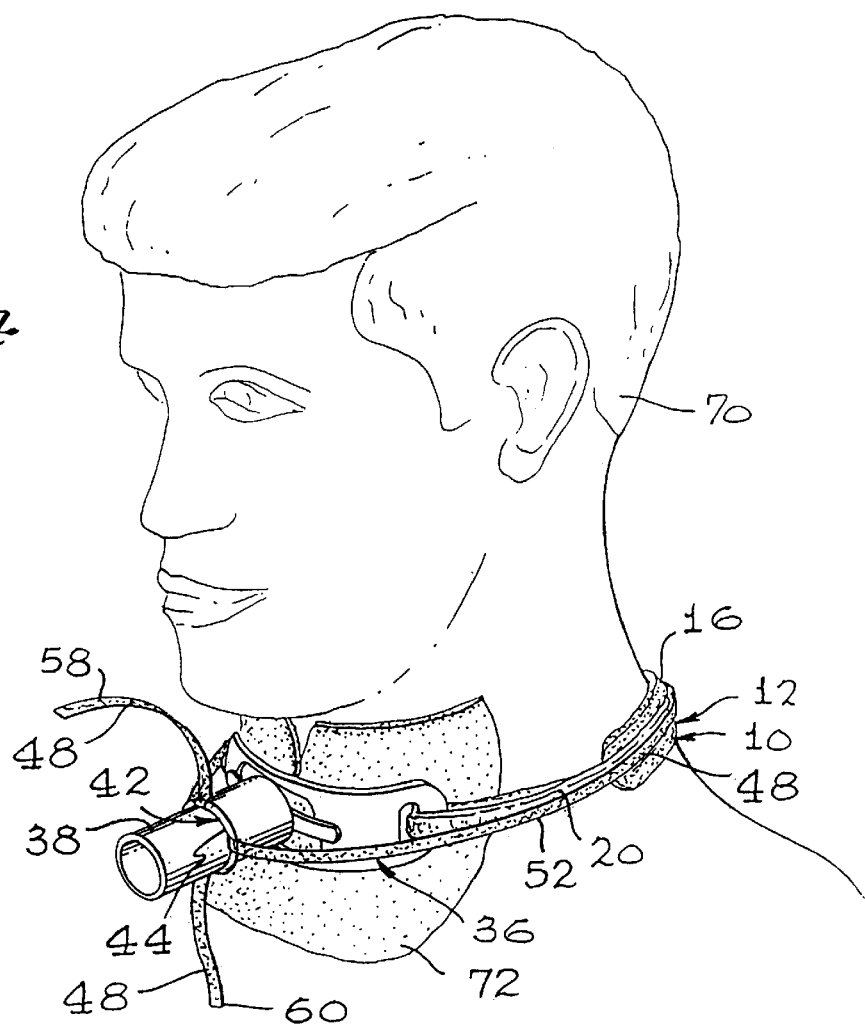
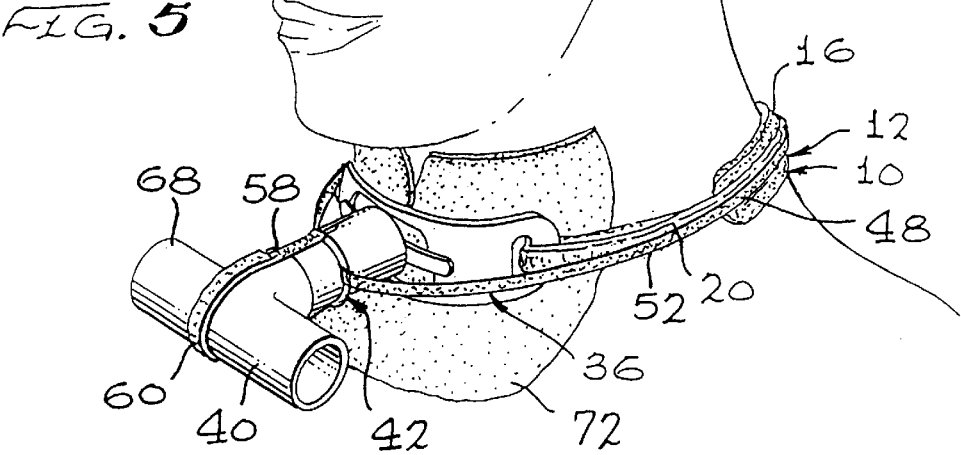

ENDOTRACHEAL TUBE ANTI-DISCONNECT DEVICE

BACKGROUND OF THE INVENTION

1. Field of the Invention

The present invention generally relates to medical devices and more particularly to an improved type of device for securely holding an endotracheal tube against a patient so that the tube cannot be easily disconnected.

2. Prior Art

Various types of devices have been used in the past to releasably secure an endotracheal tube in place against a patient. One such device comprises an elongated elastic neck band with tabs on its opposite ends adapted to pass through slots in an endotracheal tube bracket and be reflected back over the neck band for securing to the same.

However, such device has certain deficiencies. Thus, it is easily possible to inadvertantly stretch the neck band so tight so as to place a strain on the patient's neck and/or impair vital blood circulation, particularly since in many cases the patient is groggy or comatose and not able to complain about the pressure on the neck. Moreover, because of the shape of the endotracheal tube bracket and because the band merely directs the securing force in a horizontal front to rear direction, tilting of the endotracheal tube can occur as the patient moves, thus dislodging full secure emplacement of the endotracheal tube.

More complicated endotracheal tube-securing devices have also been devised but are relatively expensive, difficult to install and still do not provide positive securement of the endotracheal tube.

It is conventional to use endotracheal tubes which consist of two parts, namely, a front to rear aligned first portion, the rear end of which is inserted into the patient and a transverse second tube portion which is outside the patient and rigidly secured to the front end of the first portion of the tube.

Most endotracheal tube-securing devices do not provide means for stabilizing the position of the transverse portion of the endotracheal tube, so that some undesired rotation or other movement of the endotracheal tube can occur as the patient moves.

Accordingly, there is a need for an improved type of endotracheal tube-securing device which positively secures the endotracheal tube in place against a patient to prevent any movement of the endotracheal tube. Such device should be simple to make and use, easy to install and remove and should be relatively inexpensive and reusable, if desired.

SUMMARY OF THE INVENTION

The improved endotracheal tube anti-disconnect device of the present invention satisfies all the foregoing needs. Thus, the device is simple, inexpensive, easy to install and remove and holds the endotracheal tube securely against the patient, preventing any movement of the endotracheal tube during its use. Moreover, the device places no undue strain on the patient's neck.

The device comprises, in combination, a flexible, resilient neck band which preferably is inelastic, and an anti-disconnect ring assembly which is releasably secureable to the neck band. The neck band has an elongated body having front and rear surfaces, that is, outer and inner surfaces, and two opposite ends, each having front and rear surfaces. The front surface of each said end bears a plurality of small hooks. The ends are adapted to be passed through slots in the sides of an endotracheal tube bracket and to be reflected back over the neck band for releasable attachment thereto, the front surface of the neck band being formed of a hook-receiving material. Thus, the neck band provides means for releasably securing the endotracheal tube against forward-rearward movement.

The anti-disconnect ring assembly provides second means for stabilizing the front-to-rear position of the endotracheal tube against the patient and preventing rotation of the transverse portion of the endotracheal tube. In this regard, the assembly comprises, in combination, a ring which is adapted to be slip-fitted over the front-to-rear first portion of the endotracheal tube to help hold it in place, and also includes a plurality, preferably four, of elongated flexible resilient tabs, wings or arms.

Thus, first and second horizontal wings of the assembly have one end connected to the ring and extend horizontally outwardly from the ring on opposite sides thereof. The wings have front and rear surfaces, the rear surfaces bearing a plurality of hooks for releasably securing to the front surface of the neck band to hold the ring in place around the endotracheal tube.

First and second elongated flexible resilient vertically extending arms are connected at one end to the top and bottom, respectively, of the ring. Both arms have front and rear surfaces. One arm has a hook-receiving front surface comprising a plurality of loops and the other arm has a rear surface bearing a plurality of hooks. These arms are adapted to wrap around the transverse portion of the endotracheal tube and to be relasably secured to each other to prevent movement of the transverse portion of the endotracheal tube.

Preferably, the neck band, ring, wings and arms are formed of plastic. In one embodiment the wings are longer than the arms, in order to assure secure attachment of the wings to the neck band, the arms not being of as great a length because they wrap around the transverse portion of the endotracheal tube which is adjacent the ring when the device is used.

Further features of the improved device of the present invention are set forth in the following detailed description and accompanying drawings.

DRAWINGS

Figure 3:
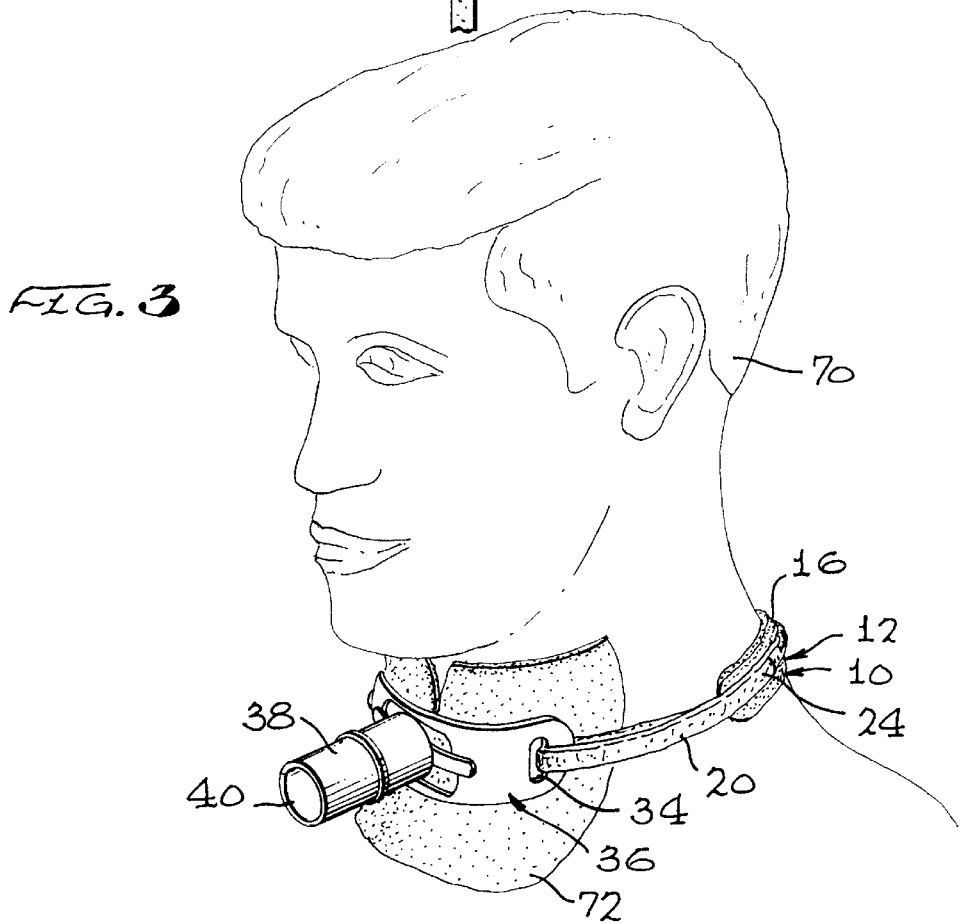
FIG. 3 is a schematic front perspective view of a patient wearing a preferred embodiment of the neck band of the present invention, with the neck band being secured to the bracket of an endotracheal tube.

FIG. 4 is a schematic front perspective view of a patient wearing the neck band of FIG. 3, and with a preferred embodiment of the ring of the assembly of the present invention secured over the front-to-rear portion of an endotracheal tube and also secured to the front or outer surface of the neck band; and, FIG. 5 is a schematic front perspective view of a patient with a preferred embodiment of the device of the present invention fully installed around an endotracheal tube, with the neck band of FIG. 3 and the ring of FIG. 4 in place and with the arms of the ring assembly wrapped around the transverse portion of the endotracheal tube.

DETAILED DESCRIPTION OF THE PREFERRED EMBODIMENT OF THE INVENTION

Figure 1:
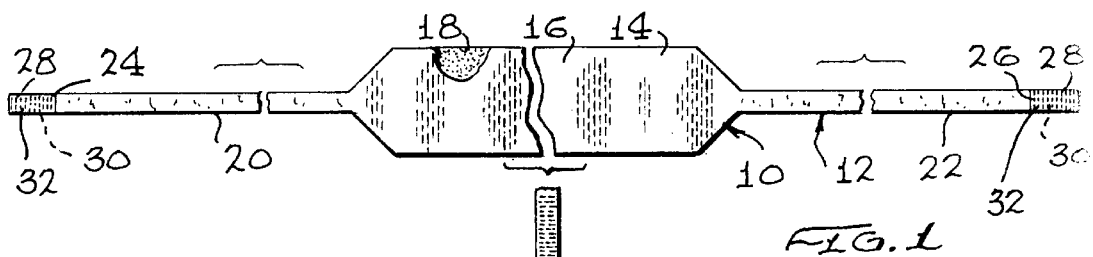
FIG. 1 is a schematic front elevation of a preferred embodiment of the neck band portion of the endotracheal tube anti-disconnect device of the present invention.

FIGS. 1 and 3:

Now referring more particularly to FIGS. 1 and 3 of the drawings, a preferred embodiment of the neck band of the endotracheal tube anti-disconnect device of the present invention is schematically depicted in front elevation. Thus, neck band 10 of device 12 is shown. Neck band 10 comprises an elongated, flexible, resilient inelastic main body 14 having opposite front and rear surfaces 16 and 18, respectively. Rear surface 18 is soft and smooth for proper comfort when applied to a patient. Front surface 16 is formed of hook-retaining material comprises a plurality of small loops (not shown) of conventional nature.

Main body 14 has two opposite end portions 20 and 22 comprising narrow elongated, flexible, resilient inelastic tabs 24 and 26 having front and rear surfaces 28 and 30. Front surfaces 28 bear a plurality of hooks 32 for releasably securing tabs 24 and 26 to front surface 16 of body 14 after passing tabs 24 and 26 through slots 34 in endotracheal tube bracket 36 (FIG. 3) and reflecting tabs 24 and 26 back onto front surface 16 of body 14. Thus, tabs 24 and 26 are used to cinch bracket 36 to the front of the patient and properly and firmly position and hold the front-to-rear portion 38 of endotracheal tube 40 (FIG. 3) in place against the patient.

Tabs 24 and 26 preferably are integral with main body 14 of neck band 10 and the entire neck band 10 is preferably formed of plastic. Although neck band 10 is preferably of inelastic material for the reasons previously specified herein, it is possible to utilize a stretchable material for neck band 10, provided care is used in applying neck band 10 to the patient.

Figure 2:
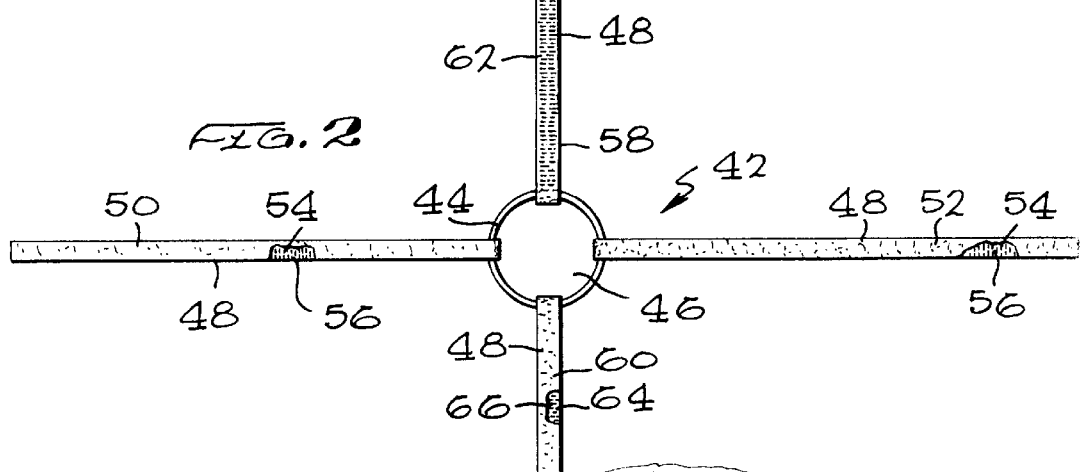
FIG. 2 is a schematic front elevation of a preferred embodiment of the ring assembly portion of the endotracheal tube anti-disconnect device of the present invention.

FIGS. 2, 4 and 5:

Now referring more particularly to FIG. 2, an improved ring anti-disconnect assembly 42 is shown which comprises, in combination, a ring 44 with central space 46 and a plurality of, in this instance four, flexible, resilient, elongated connectors 48, preferably of plastic or the like, one end of each of which is connected to ring 44 with each connector 48 extending outwardly from ring 44. Of the connectors 48, two are horizontally disposed wings 50 and 52, the rear surfaces 54 of which bear a plurality of hooks 56 for releasably securing wings 50 and 52 to opposite sides of the front surface 16 of neck band 10, as shown in FIGS. 4 and 5.

Ring 44 is dimensioned to be slip fitted over portion 38 of endotracheal tube 40 and be pulled tightly against bracket 36 by wings 50 and 52, thus anchoring ring 44 to bracket 36 and holding portion 38 releasably but firmly in place against a patient.

Ring 44 also bears two vertically disposed connectors 48, namely, arms 58 and 60. The front surface 62 of upper arm 58 is of hook-receiving and holding looped material while the rear surface 64 of lower arm 60 has a plurality of hooks 66 to enable arms 58 and 60 to be releasably secured together after wrapping them around the horizontally extending portion 68 of endotracheal tube 40 in order to further stabilize tube 40 in a fixed position. Arms 58 and 60 have the additional advantage, when tightly cinched around portion 68, of preventing rotation of portion 68 during movement of the patient.

FIGS. 3,4 and 5 illustrate steps in connecting the anti-disconnect device 12 to endotracheal tube 40 and to the patient, with FIG. 5 showing device 12 in the fully assembled operational condition. For purposes of clarity transverse portion 68 of tube 40 is not shown, except in FIG. 5. Moreover, FIGS. 3,4 and 5 illustrate a patient 70 wearing a gauze backing 72 between bracket 36 and the patient's throat, as is conventional.

It will be understood that device 12 can be fabricated of components other than or in combination with plastic. For example, ring 44 can be of rubber, wood, metal or the like, while neck band 10 can be of cloth, inelastic rubber or the like, as can tabs 24 and 26 and connectors 48.

Further features of the improved device of the present invention, its components and parameters, as are within the scope of the appended claims form part of the present invention.

What is claimed is:

1. An improved endotrachial tube anti-disconnect device, said device comprising, in combination:

a) a flexible, resilient neck band having an elongated body having front and rear surfaces, said front surface bearing hook-receiving means, said body having having two opposite ends, each said end having front and rear surfaces, the front surface of each said end bearing a plurality of hooks adapted to be releasably passed through slots in an endotrachial tube connector and being adapted to be releasably secured to said front surface of said body to hold said connector in place against a throat; and, b) an anti-disconnect ring assembly, said assembly comprising, in combination:

i. a ring having a central endotracheal tube-receiving space, said ring thereby being adapted to fit around an endotracheal tube, ii. first and second horizontally extending flexible resilient wings connected to said ring and extending outwardly from opposite sides of said ring, said wings having front and rear surfaces, said rear surfaces of said wings bearing a plurality of hooks adapted to being releasably secured to said front surface of said body of said neck band to hold said ring against said neck band body, and, iii. first and second flexible resilient vertically extending arms connected to opposite top and bottom portions of said ring, said first arm having front and rear surfaces, the front surface of which bears hook-receiving means, said second arm having front and rear surfaces, the rear surface of which bears a plurality of hooks, said arms being adapted to wrap around an endotracheal tube and to releasably connect to each other to hold said endotracheal tube in place.

2. The improved endotracheal tube anti-disconnect device of claim 1 wherein said neck band, wings and arms are inelastic and are of plastic.

3. The improved endotracheal tube anti-disconnect device of claim 1 wherein said wings are of greater length than said arms.

4. The improved endotracheal tube anti-disconnect device of claim 1 wherein said ring is of plastic and dimensioned to slip fit over an endotracheal tube.

\* \* \* \* \*